United States Patent

Wei et al.

Patent Number: 6,123,912
Date of Patent: Sep. 26, 2000

[54] PROCESS FOR PRODUCING ALUMINA MATERIAL FOR ARTIFICIAL SKELETON WITH HIGH STRENGTH

[75] Inventors: Wen-Cheng J. Wei, Taipei; Shui-jin Cheng, Hsinchu; Chang-Li Hsieh, Kaohsiung; Hung-Chan Kao, Taichung, all of Taiwan

[73] Assignee: National Science Council, Taipei, Taiwan

[21] Appl. No.: 09/233,709

[22] Filed: Jan. 19, 1999

[30] Foreign Application Priority Data

May 6, 1998 [TW] Taiwan .................................. 87107027

[51] Int. Cl.⁷ ....................................................... C01F 7/02
[52] U.S. Cl. ...................... 423/625; 252/308; 252/313.1; 252/351; 252/352; 264/21; 264/645; 264/681; 501/127
[58] Field of Search ............................ 423/625; 252/308, 252/313.1, 351, 352; 264/21, 645, 681; 501/127

[56] References Cited

U.S. PATENT DOCUMENTS

| | | |
|---|---|---|
| 3,871,031 | 3/1975 | Boutin . |
| 3,905,047 | 9/1975 | Long . |
| 4,396,595 | 8/1983 | Heytmeijer et al. ............. 423/625 |
| 4,917,702 | 4/1990 | Scheicher et al. ............. 623/16 |
| 4,952,389 | 8/1990 | Szymanski et al. ............. 423/625 |
| 5,066,625 | 11/1991 | Philipp ............................. 501/127 |
| 5,518,660 | 5/1996 | Wei et al. ..................... 252/313.1 |
| 5,580,832 | 12/1996 | Malghan et al. ................. 501/1 |
| 5,716,565 | 2/1998 | Stangle et al. ................. 264/56 |

OTHER PUBLICATIONS

ISO 6474:1994(E).
L. L. Hench and D. R. Ulrich, "Ultrastructure Processing of Ceramics, Glasses, and Composites," John Wiley & Sons, pp. 407–417, 1984.
J. Cesarano III, and I. A, Aksay, "Stability of Aqueous $\alpha$–$Al_2O_3$ Suspensions with Poly(methacrylic acid) Polyelectrolyte," J. Am. Ceram. Soc., 71(4), pp. 250–255, 1998.
J. S. Reed, "Introduction to the Principles of Ceramics Processing," John Wiley & Sons, pp. 139–141, 1988.
J. Cesarano III, and I. A. Aksay, "Processing of Highly Concentrated Aqueous $\alpha$–Alumina Suspensions stabilized with Polyelectrolytes," J. Am. Ceram. Soc., 71(12), pp. 1062–1067, 1988.
B. V. Velamakanni and F. F. Lange, "Effect of Interparticle Potentials and Sedimentation on Particle Packing Density of Bimodal Particle Distributions During Pressure Filtration," J. Am. Ceram. Soc., 74(1), pp. 166–172, 1991.
M. Kumagai and G. L. Messing, "Enhances Densification of Boehimite Colloidals by $\alpha$–Alumina Seeding," Comm. Am. Ceram. Soc., C230–31, 1984.

Primary Examiner—Tom Dunn
Assistant Examiner—Cam N. Nguyen
Attorney, Agent, or Firm—Laff, Whitesel & Saret, Ltd.; J. Warren Whitesel

[57] ABSTRACT

A process for producing an alumina material with high strength is disclosed. The process for producing an alumina material includes the steps of (a) providing a solution containing a dispersing agent, (b) mixing a $\theta$-alumina powder and an $\alpha$-alumina powder with the solution to form a slurry, (c) filtering the slurry to form a green part, (d) drying the green part, and (e) densifying the dried green part to form the alumina material.

19 Claims, 6 Drawing Sheets

PROCESS FOR PRODUCING ALUMINA MATERIAL FOR ARTIFICIAL SKELETON WITH HIGH STRENGTH

FIELD OF THE INVENTION

The present invention relates to a process for producing an alumina material with high strength, and especially to a process for producing an alumina artificial skeleton.

BACKGROUND OF THE INVENTION

In the field of the prosthesis, the application of the artificial hipjoint is the most difficult task because the hipjoint must not only bear a load but also exercise as a function of bearing. Therefore, the material of the artificial hipjoint must have high strength and high toughness. On the other hand, the contact surface of an artificial hipjoint must also have high wearability for the daily wear.

The osteolysis is the most serious problem in the application of the artificial skeleton. The metal-polymer composite is commonly used in prosthesis, but the wear of the polymer used for the artificial hipjoint results in a generation of the scraps which will be absorbed by the human body. Therefore, the metal-polymer artificial hipjoint, implanted in a human body, has to be replaced every few years. The biomedical material engineers find out that the ceramic with its chemical stability, high wearability, and high strength is a good material to replace the polymer part of the composite. By minimizing the scraps, the osteolysis is lessened and the use of the metal-ceramic composite in the human body has already obtained a good clinic result.

The usage of alumina in the artificial skeleton is not a new subject (U.S. Pat. Nos. 3,871,031 and 3,905,047). The ISO 6474:1994(E) has defined the physical and chemical properties of the alumina material in detail, such as the composition, design, mechanical strength, and testing methods, and many papers have been published in this field. If the alumina prosthesis can consist with the standards, it is allowed to be used in a human body clinically.

The alumina powder used for the prosthesis has to be very fine (submicro) and pure (>99.8%) for the green compact after sintering to have a homogeneously fine grain structure without large internal defects (>5 $\mu$m) to obtain high strength. The conventional process for producing the alumina material is powder metallurgy. However, the cost for producing an alumina skeleton by powder metallurgy is high because of the complex processes, including the cold isotropic pressing, hot isotropic pressing, and mechanical polishing. The technique for producing an alumina skeleton is difficult, too. It is hard to compact the fine powder by conventional compacting methods to obtain a high density because of the agglomeration and low flowability of fine powders. The material produced by this method does not have good mechanical property and microstructure. (L. L. Hench and D. R. Ullrich, "Ultrastructure Processing of Ceramics, Glass, and Composites", John Wiley & Sons, pp. 407–417, 1984)

The colloidal process is another process for producing the artificial skeleton. It uses a slurry to form the green part. By adding a dispersing agent to the slurry and controlling its pH value, the electrostatic repulsion and steric hindrance make the particles in the slurry have a good dispersion, even submicro particles, and the green part can have a high strength (J. Cesarno III, and I. A. Aksay, J. Am. Ceram. Soc., 71(4), pp. 250–255, 1998). Although the colloidal process is a good process for producing a fine powder ceramic material, there are many factors affecting the process as follows:

(1) The Surface Potential:

The ceramic powder has a large specific surface area and a poor solubility and, therefore, the powder is easily induced to have a charge. The negative particles attract positive particles and repel particles with same charges because of the Coulombic force. Although the slurry is neutral in electricity, there are potential differences on the particles. If an electric field is applied to the slurry, the particles will move electrophoretically and a part of the slurry adsorbed by the particles will also move. (J. S. Reed, Introduction to the Principles of Ceramics Processing, John Wiley & Sons, 1988)

(2) The pH Value of the Slurry:

The pH value of the slurry can affect the surface charges of the particles. The degree of ionization is changed with the pH value, and the ionization makes the electric steric effect between the alumina particles more serious.

(3) The Dispersing Agent:

The polymethacrylic acid (PMAA) and polyacrylic acid (PAA) are the most popular and effective dispersing agents used in the alumina slurry. The dispersing agents cause the particles in the slurry to have a better dispersion because of the large electrosteric effect. (J. Cesarno III, and I. A. Aksay, J. Am. Ceram. Soc., 71(12), pp. 1062–1067, 1988)

(4) The Flowing Behavior:

The viscosity of the slurry is a critical factor in its flowability. If the viscosity of the slurry is too low, the sedimentation of the particles will induce the particles to segregate. If the viscosity is too high, the bubbles in the slurry will not come out easily. (B. V. Velamakanni and F. F. Lange, J. Am. Ceram. Soc., 74(1), pp. 166–172, 1991)

(5) The Shape of the Particles:

When the aspect ratio of the powder increases, the green density will decrease. The material made by the powder with the aspect ratio equals to one (equi-axial) will have the highest green density.

(6) The Particle Size Distribution:

By carefully controlling the particle size distribution of the powder, the small particles can fill in the interspace of the large particles and the green density can be effectively raised.

Because the colloidal process can effectively mix particles with different sizes to produce a uniform ceramic green part, the sintering density of the green part is increased. There has been reported that the $\alpha$-alumina can improve the phase transformation of the boehmite and the $\theta$-alumina during the sintering process. By adding a little amount of the $\alpha$-alumina to the $\theta$-alumina slurry, the sintering rate and the sintering density are increased. Although the reason is still unknown, this discovery is very important for controlling the sintering rate and the microstructure of the $\theta$-alumina (M. Kumagai and G. L. Messing, "Enhanced densification of boehmite colloidals by $\alpha$-alumina seeding", Comm. Am. Ceram. Soc., C230–31, 1984).

The main concern of the present invention is to provide a process for producing an alumina material with high strength which is suitable to be used in the artificial skeleton.

SUMMARY OF THE INVENTION

An object of the present invention is to provide a process for producing an alumina material with high strength and homogeneous microstructure.

The process according to the present invention includes the steps of a) providing a solution containing a dispersing agent, b) mixing a $\theta$-alumina powder and an $\alpha$-alumina powder with the solution to form a slurry, c) filtering the slurry to form a green part, d) drying the green part, and e) densifying the dried green part to form the alumina material.

In accordance with the present invention, the θ-alumina powder has a purity higher than 99.6%, a specific surface area larger than 32.0 m$^2$/g, and an average diameter smaller than 0.4 μm. The α-alumina powder has an average diameter smaller than 1.0 μm and a content ranged from 1.0 to 20.0 wt %. The dispersing agent is one of a semicarbazide hydrochloride (S-HCl) and an ammonium salt of polymethacrylic acid (PMAA-N) and the solution is an aqueous solution. Besides, the slurry in the step (d) is filtered under a pressure ranged from 2.5 to 40.0 atm. The step (e) is executed by sintering at a temperature ranged from 1500 to 1600° C. for 1 to 4 hours. The alumina material has a relative density over 98.5%, a average strength over 450 MPa, an average grain size less than 4 μm, and an equi-axial crystalline microstructure.

Another object of the present invention is to provide a process for producing an alumina artificial skeleton with high strength and homogeneous microstructure.

The process according to the present invention includes the steps of a) providing a solution containing a dispersing agent, b) mixing a θ-alumina powder and a nucleation-controlling agent with the solution to form a slurry, c) filtering the slurry to form a green part, d) drying the green part, and e) sintering the dried green part to form the alumina artificial skeleton.

Another further object of the present invention is to provide a process for producing an alumina artificial skeleton with high strength. The process includes the steps of a) providing a solution containing a dispersing agent, b) mixing a θ-alumina powder and a nucleation-controlling agent with the solution to form a slurry, c) pouring the slurry into a mold having a shape of the artificial skeleton, d) filtering the slurry to form a green part, e) releasing the green part from the mold, f) drying the green part, and g) sintering the dried green part to form the high strength alumina artificial skeleton.

Preferably, the nucleation-controlling agent is an α-alumina powder. The artificial skeleton is a head of a hipjoint.

The present invention may best be understood through the following description with reference to the accompanying drawings, in which:

DETAILED DESCRIPTION OF THE PREFERRED EMBODIMENTS

The θ-alumina powder used in the present invention is available from American Ceralox company, designated by APA-0.2. This powder has a high purity (>99.6%), a small diameter ($d_{50}$=0.2 μm), and a large specific surface area (34–41 m$^2$/g). Two kinds of α-alumina powders used in the present invention are A-16SG and AKP-30, available from Alcoa and Sumitomo Chemical respectively, both of which have a larger diameter ($d_{50}$=0.4 μm) than that of APA-0.2. Besides, there are two kinds of dispersing agent used in the present invention, semicarbazide hydrochloride (S-HCl) and ammonium salt of polymethacrylic acid (PMAA-N). Now, the preferred embodiments of the present invention are described in detail as follows.

Embodiment 1

Figure 1:
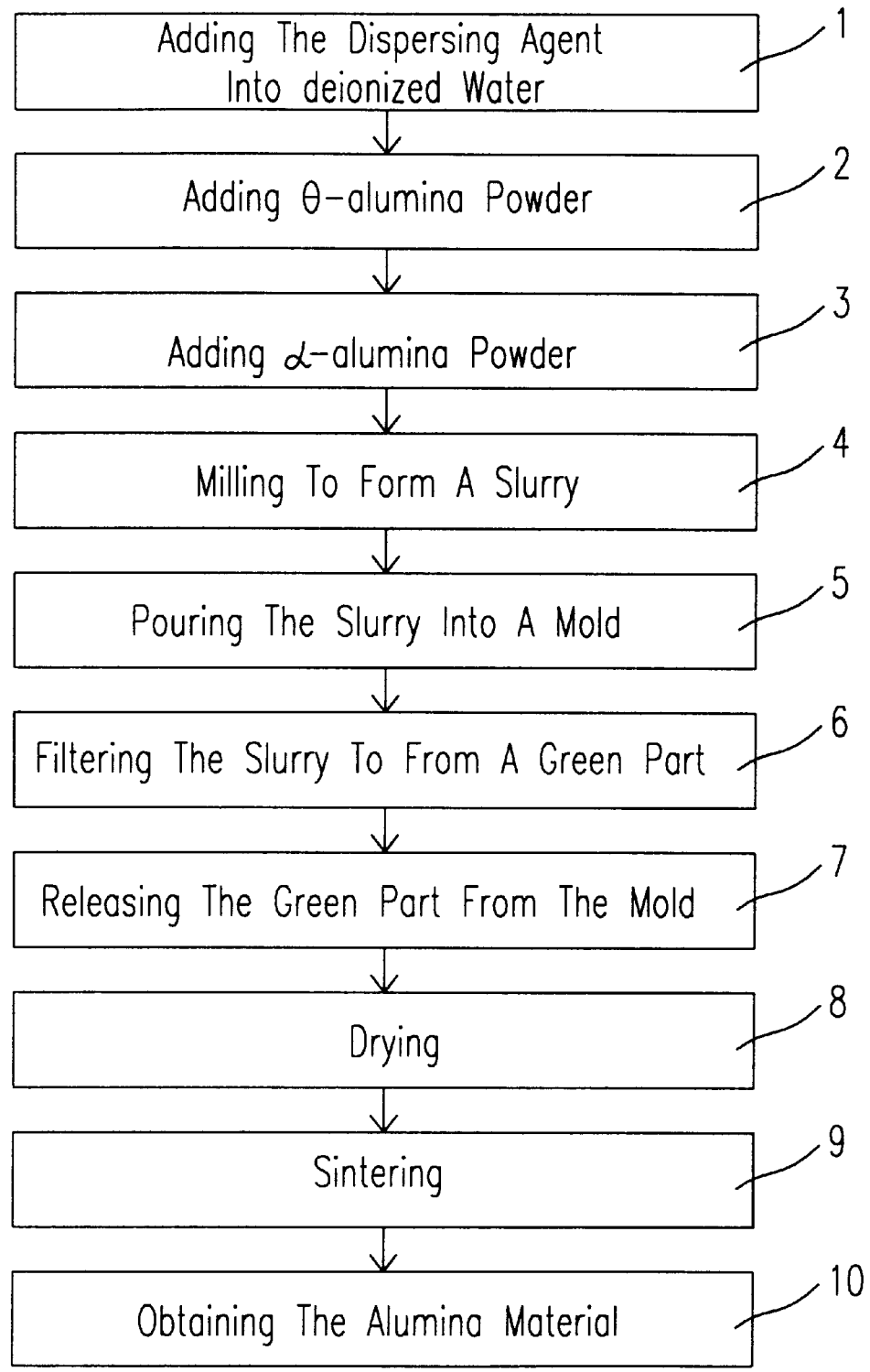
FIG. 1 is a flowchart showing a process for producing an alumina material according to the present invention.

The composition of A-series slurry (100 ml) is: 70 ml water, 96.984 g APA-0.2 (θ-alumina powder), 11.958 g A-16SG (α-alumina powder), and 2.17 g S-HCl. S-HCl is dispersing agent. A-16SG is replaced by AKP-30 in the slurry of the K-series. The A'-series slurry uses PMAA-N to replace the S-HCl as the dispersing agent, and the same weight (2.178 g) is used. FIG. 1 shows the colloidal process for producing the alumina material according to the present invention. The process is as follows.

Step 1: The dispersing agent is added in a bottle containing deionized water.

Step 2: The θ-alumina powder and the ZrO$_2$ milling balls are added into the bottle and are milled for 1 hour.

Step 3: The α-alumina powder is added.

Step 4: The bottle of water and powders is milled for 6 to 24 hours to form a slurry.

Step 5: The slurry is filtered by a 200 mesh sieve. Then, the slurry is poured into a mold (a porous copper matrix material having a filter paper thereon) after vacuum degassing.

Step 6: A green part is formed by pressure filtration and the filtering pressure is 10 atm.

Step 7: The green part is released from the mold after natural drying.

Step 8: The green part is dried at 40° C. for two days, 60° C. for one day, and 105° C. for another one day in an oven to form a dried green part. The density of the dried green part is measured by Archimedean method, wherein the density of the dried green part divided by the theoretical density of the green part (the theoretical density of the θ-alumina is 3.580 g/cm$^2$ and that of the α-alumina is 3.986 g/cm$^2$) is called as the relative green density. The relative green density is listed in Table 1.

TABLE 1

Relative green density of different kinds and contents of the green parts with different kinds of dispersing agents. The error is ± 0.2%.

| Content of the α-seed (wt. %) | A-series (the dispersing agent is S—HCl) | K-series (the dispersing agent is S-HCl) | A'-series (the dispersing agent is PMAA-N) |
|---|---|---|---|
| 0.00 | 54.2 |  | 46.3 |
| 0.01 | 54.8 | 54.7 |  |
| 0.02 |  | 55.4 |  |
| 0.05 | 55.7 | 55.6 | 48.2 |
| 0.08 | 55.6 | 55.7 |  |
| 0.10 | 55.6 | 55.7 |  |
| 0.12 | 55.6 |  |  |
| 0.15 | 55.8 | 55.9 | 49.7 |
| 0.20 | 56.1 |  |  |
| 0.40 |  |  | 51.7 |

It is easy to identify the packing efficiency according to the relative density of the green part. The surface force influences the dispersing condition of the particles in the slurry, and the viscosity affects the flowability of the slurry. If the surface force is lowered and the viscosity is increased, the density of the green part will decrease due to poor packing. In the present invention, the 5% to 15% A-16SG (α-alumina powder) with S-HCl (dispersing agent) can have the highest relative density of 55.7±0.2%. The AKP-30 (α-alumina powder) with S-HCl (dispersing agent) can also have the best relative density of 55.7±0.2%. This density is higher than that without α-seed (54.2%). Besides, the densities of A-series are all in the range of 55.7±0.1% when adding 5% to 15% A-16SG. This is a great discovery because the dimension stability is very helpful for controlling the size of the green part after sintering.

Figure 2:
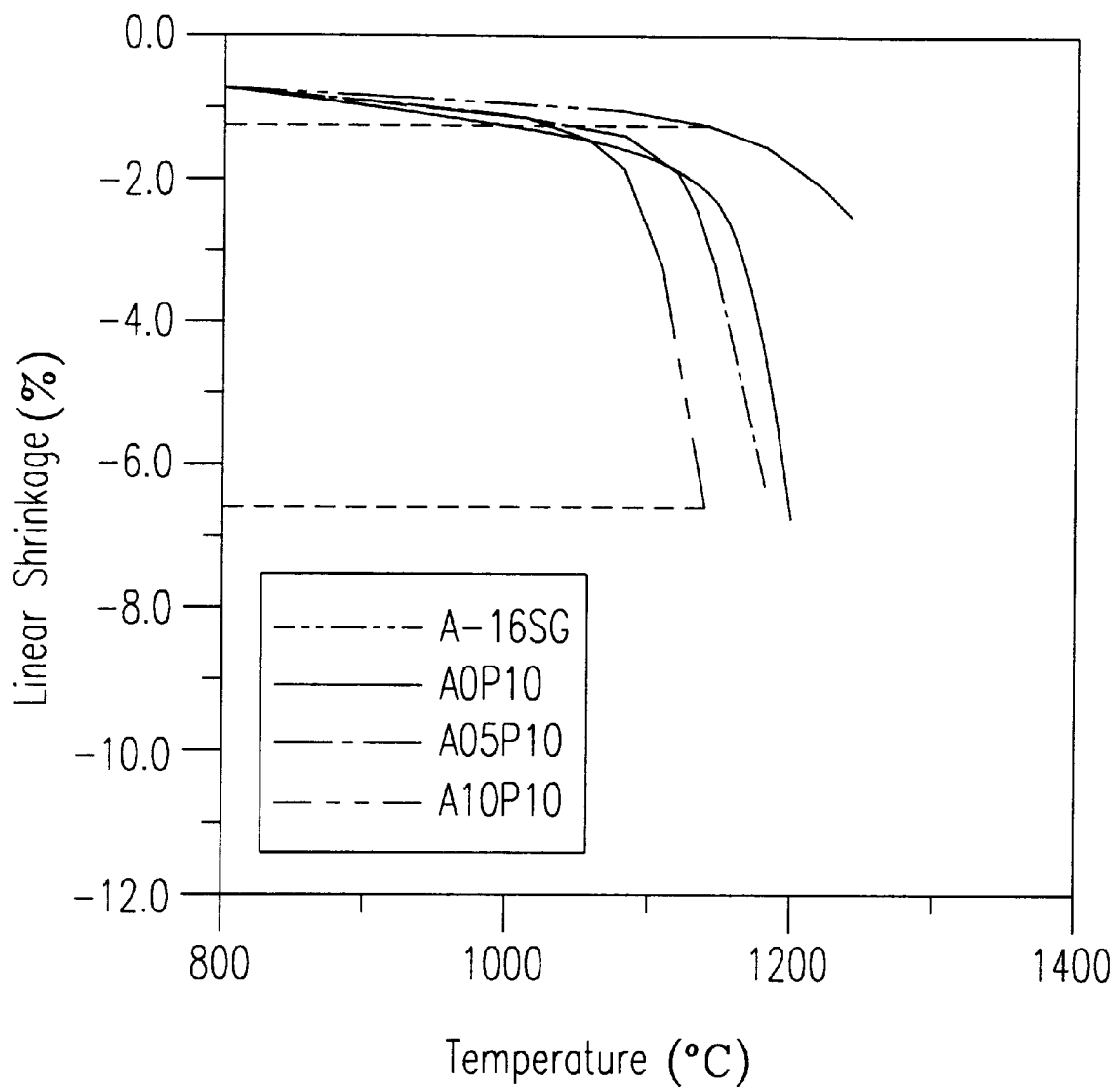
FIG. 2 is a shrinkage-to-temperature diagram of alumina green parts with various amount of A-16SG.

The green parts are cut into 20×5×5 mm³ samples to be heated. The heating rate is 5° C./min and the temperature is ranged from 800° C. to 1200° C. The A-series samples, A0, A05, and A10, are made by 0%, 5%, 10% A-16SG powder respectively and the A-16SG is made by pure A-16SG powder for comparison. The filtering pressure is 10 atm. FIG. 2 is a shrinkage-to-temperature curve, measured by a dilatometer (single-push-rod dilatometer, Theta Co., USA), wherein the A10P10 sample has the largest shrinkage. It proves that the addition of α-seed is conducive to increase the sintering rate and lower the sintering temperature.

Step 9 : The dried green part is put in the crucible and is sintered under 1 atm. The process is as follows:
from room temperature to 1000° C. by a heating rate of 10° C./min;
from 1000° C. to 1100° C. by a heating rate of 2° C./min;
from 1100° C. to 1550° C. by a heating rate of 10° C./min;
at 1550° C. for 2 hours;
from 1550° C. to room temperature, a cooling rate of 30° C./min.

Step 10: The alumina material with high strength is obtained. Table 2 shows the sintering densities of the alumina materials. The A-series, using S-HCl as the dispersing agent, has the highest density of 99.3±0.2% when adding 10% α-seed therein. The K-series, using S-HCl as the dispersing agent, has the second highest density of 99.1±0.1% when adding 2% α-seed therein.

TABLE 2

Relative sintering densities of different kinds and contents of the sintered samples. The error is ± 0.2%. (sintering temp = 1550° C., sintering time = 2 hr, filtering pressure = 10 atm)

| Content of the α-seed (wt. %) | A-series (the dispersing agent is S—HCl) | K-series (the dispersing agent is S-HCl) | A'-series (the dispersing agent is PMAA-N) |
|---|---|---|---|
| 0.00 | 99.1 | — | 96.5 |
| 0.01 | 98.7 | 98.2 | — |
| 0.02 | — | 99.1 | — |
| 0.05 | 98.8 | 98.9 | 98.3 |
| 0.08 | 99.0 | 98.7 | — |
| 0.10 | 99.3 | 98.6 | — |
| 0.12 | 98.8 | — | — |
| 0.15 | 98.6 | 97.6 | 98.9 |
| 0.20 | 97.4 | — | — |
| 0.40 | — | — | 97.8 |

Embodiment 2

Figure 3:
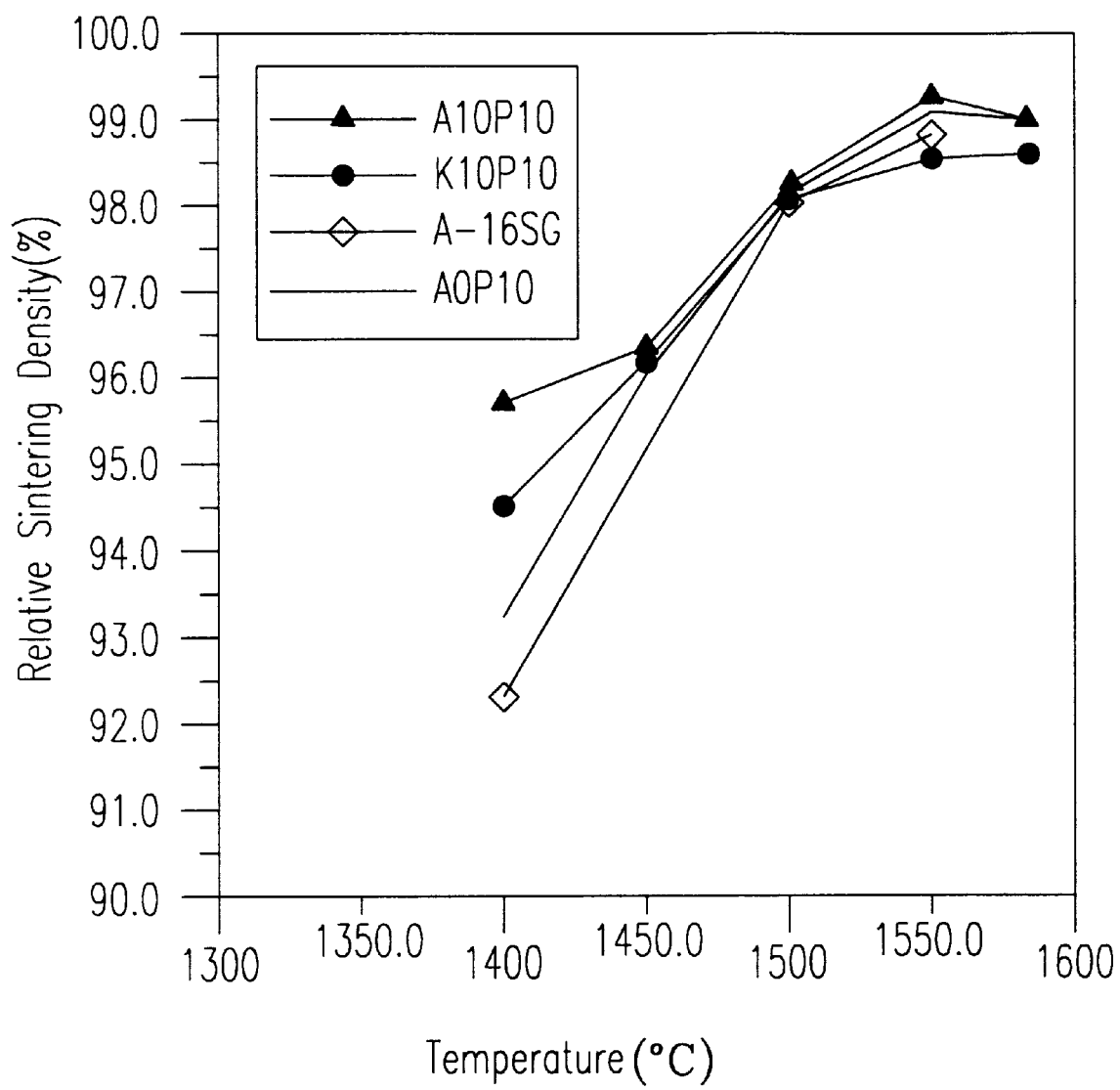
FIG. 3 is a sintering density-to-temperature diagram of alumina green parts according to the present invention.

The second preferred embodiment adopts the same colloidal process as the first preferred embodiment. The A-series samples, A0 and A10, are made by APA-0.2 powder with 0% or 10% A-16SG powder respectively, the K-series sample, K10, is made by APA 0.2 powder with 10% AKP-30 powder, and the A-16SG is made by pure A-16SG powder for comparison. The samples are also named as P10 in accordance with the filtering pressure (The filtering pressure is 10 atm). The densities of the samples sintered at 1400° C. to 1580° C. for 2 hours are shown in FIG. 3. The A10P10 has the highest density and this result is consisted with that of the first preferred embodiment.

Figure 4:
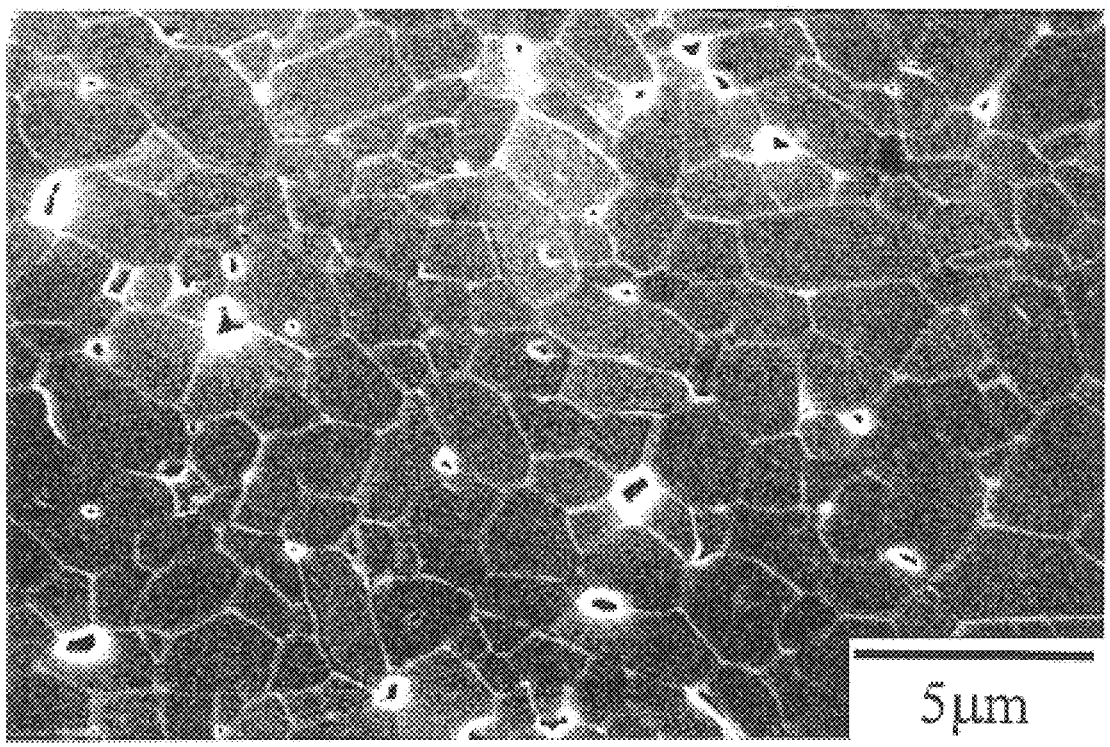
FIG. 4 shows a microstructure of the alumina material after sintering according to the present invention.

After sintering the above-mentioned samples at 1550° C. for 0.5 to 2 hours, the grain size of the samples are measured. The average grain size (at least including 200 grains) and the sintering density of the samples are shown in Table 3. The sample, A10P10, under the sintering conditions time of 2 hours has the highest density and the smallest grain size among three samples. The equi-axial microstructure of A10P10 is shown in FIG. 4.

TABLE 3

Relative sintering densities and average grain sizes of alumina materials. (R. D. = relative sintering density, G = grain size)

| | 0.5 hr | | 1.0 hr | | 2.0 hr | |
|---|---|---|---|---|---|---|
| sample | R.D. % | G(μm) | R.D. % | G(μm) | R.D. % | G(μm) |
| A0P10 | — | — | 98.5 | 2.7 | 99.1 | 3.3 |
| A10P10 | 98.5 | 2.3 | 99.0 | 2.4 | 99.1 | 3.0 |
| K10P10 | 97.0 | 2.1 | 98.7 | 2.6 | 98.9 | 4.1 |

Embodiment 3

The same procedure of the first preferred embodiment is followed. The effect of the filter pressure on the A10 and A0 samples under a filter pressure ranged from 2.5 to 60 atm are compared. The green density of the dried green part are shown in Table 4. The green densities of A10 are 55.6% under the pressure ranged from 10 to 40 atm. This discovery shows this colloidal process has good stability.

TABLE 4

Relative green densities of A0 and A10 under different filtration pressures. (R.D. = relative green density)

| filtering pressure (atm) | R.D. of A0 (%) | R.D. of A10 (%) |
|---|---|---|
| 2.5 | — | 55.4 |
| 5 | — | 56.2 |
| 10 | 54.2 | 55.6 |
| 20 | 54.2 | 55.6 |
| 30 | 54.3 | 55.6 |
| 40 | 54.3 | 55.6 |
| 50 | 54.1 | 55.4 |
| 60 | 53.9 | |

Further, the dried green part is sintered at 1550° C. for 2 hours and the relative sintering density is measured as shown in Table 5. In Table 5, A10 has the highest sintering density under a filtration pressure of 10 atm.

TABLE 5

Relative sintering densities of A0 and A10 under different filtration pressures. (R.D. = relative sintering density)

| filtration pressure (atm) | R.D. of A0 (%) | R.D. of A10 (%) |
|---|---|---|
| 2.5 | — | 98.7 |
| 5 | — | 98.9 |
| 10 | 99.1 | 99.3 |
| 20 | 99.1 | 98.9 |

TABLE 5-continued

Relative sintering densities of A0 and A10 under different filtration pressures. (R.D. = relative sintering density)

| filtration pressure (atm) | R.D. of A0 (%) | R.D. of A10 (%) |
| --- | --- | --- |
| 30 | 99.2 | 98.9 |
| 40 | 99.2 | 98.7 |
| 50 | 99.0 | 98.4 |
| 60 | 98.5 | — |

Embodiment 4

Figure 5:
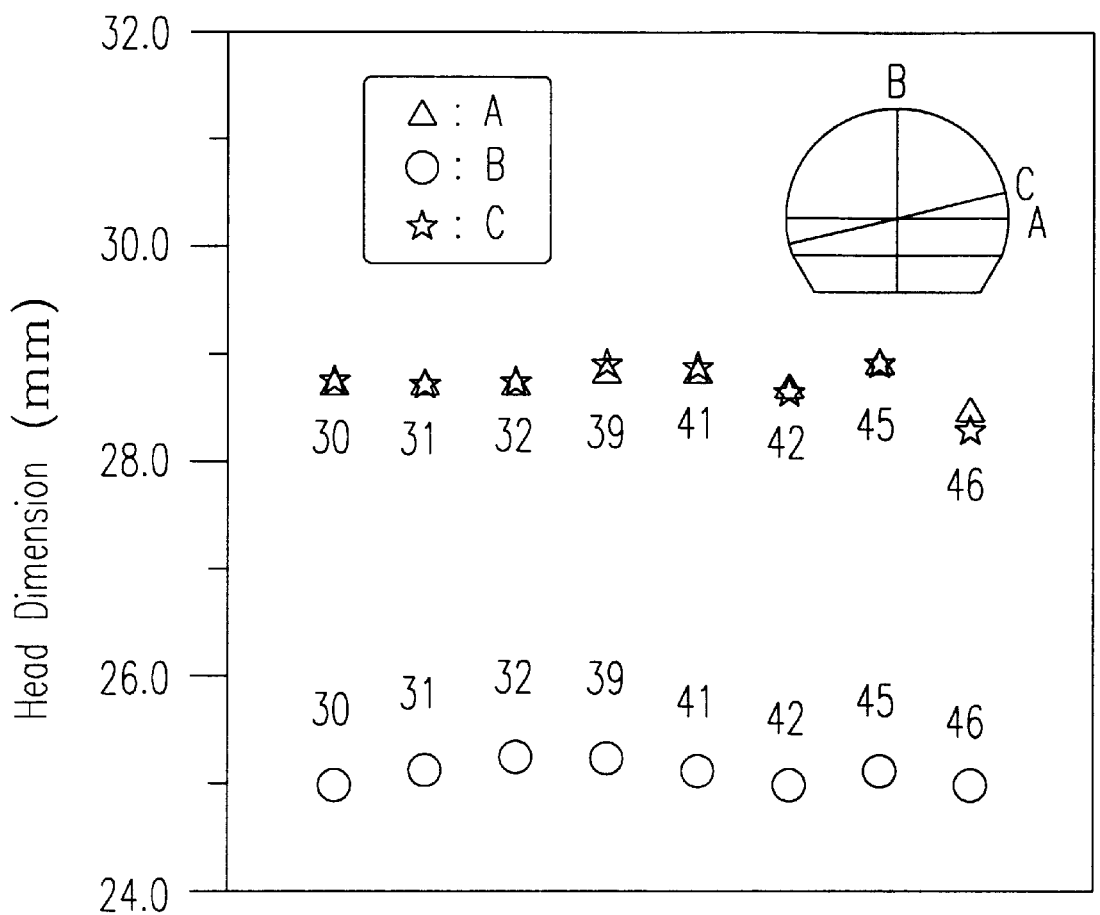
FIG. 5 is a statistical diagram showing the head size of the alumina artificial hipjoint in three directions according to the present invention.

The fourth preferred embodiment adopts the same colloidal process as the first preferred embodiment and this embodiment produces an alumina artificial skeleton. The A10 material is molded into a mold with the shape of the head of a hipjoint. The head of the hipjoint has a diameter of 36.25 mm and is consisted of three pieces of plaster casts. There is a conoid hole in the middle of the head with the angle of 5°31'30" for connecting with the bone. The plaster molds must be dried in the oven for 4 hours before each time of usage. Then, the molds are combined and fixed by clamps. Thereafter, the A10 slurry is poured into the molds and filtered under a pressure of 5 atm for 10 minutes, and then 10 atm for 2.5 to 4 hours. After the pressure filtration, the green part is released from the molds and sintered at 1550° C. for 2 hours. When the head is cooled off, the diameter (in the directions A and C) and the height (in the direction B) of the head are measured as shown in FIG. 5. The average diameter and standard deviation are shown in Table 6. The deviation in Table 6 is small and this discovery shows the dimension of the head is under good control.

TABLE 6

Average diameter and standard deviation of the alumina head in three directions.

| direction | average diameter (mm) | standard deviation (%) |
| --- | --- | --- |
| A | 28.73 | 0.26 |
| B | 28.74 | 0.23 |
| C | 25.09 | 0.45 |

Embodiment 5

Figure 6:
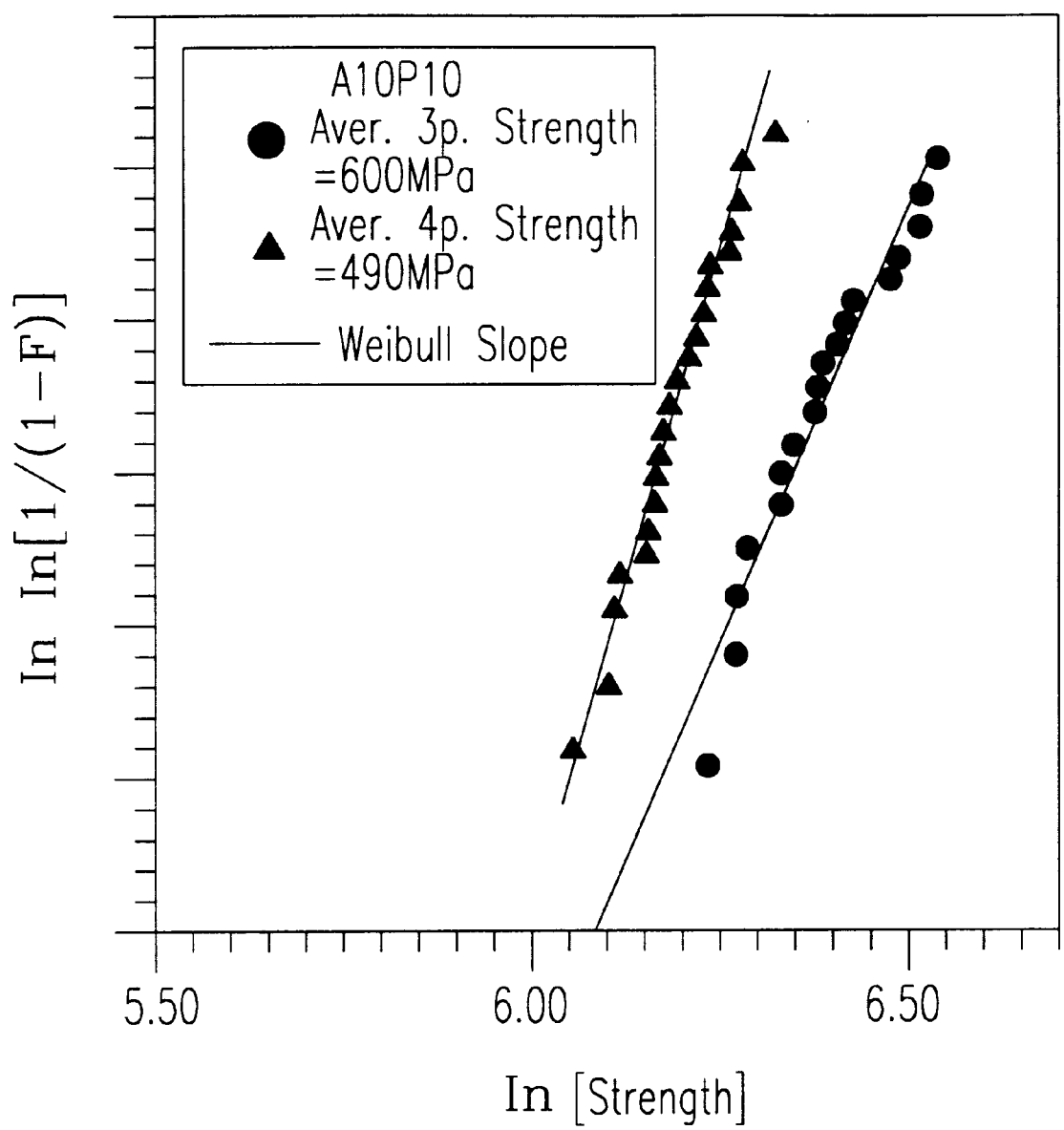
FIG. 6 is a diagram showing the strength distribution of the alumina material according to the present invention.

The A10P10 testing bar, produced under the same procedure as the first preferred embodiment, has a dimension of $4.0(\pm0.1)\times3.0(\pm0.1)\times36(\pm1.0)mm^3$. The strength of the rod is measured by three and four points bending tests by the universal testing machine (MTS810, MTS Co., USA). The mechanical strength is shown in Table 7, wherein all values of the three point bending test are higher than the standard of ISO 06474 for the alumina materials (400 MPa). FIG. 6 shows the Weibull distribution of the testing rods, wherein the abscissa specifies the strength and the ordinate specifies the probability of fracture. The slopes m of these tests are 11.2 and 17.3 respectively, and are higher than the conventional value of alumina materials which is between 7 and 10. This means that the microstructure of the alumina material according to the present invention is more uniform and homogeneous than the conventional one.

TABLE 7

Bending strength of A10P10.

| method | frequency of test | strength (MPa) average | highest | lowest | Weibull slope |
| --- | --- | --- | --- | --- | --- |
| 3 points | 18 | 600 | 695 | 513 | 11.2 |
| 4 points | 32 | 490 | 555 | 390 | 14.9 |

The advantages and characteristics of the present invention are as follows:
1. Because the θ-alumina powder has a high purity and a high specific surface area, the resulting alumina material has a fine grain structure with a high density and a higher strength;
2. The addition of α-alumina powder increases the green density;
3. The α-alumina powder is used as a nucleation agent. The nucleation agent increases the nucleation rate of the θ-alumina. Therefore, by mixing these θ-alumina powder and α-alumina powder, the resulting alumina material has a higher sintering density, a higher strength, and a finer grain size structure under a lower sintering temperature;
4. The time of filtration under a high pressure can be effectively reduced and the particle segregation resulting from the sedimentation during the filtration is also eliminated.
5. This process is capable of producing the alumina material with a complex shape and a uniform microstructure.

In brief, the process for producing an alumina material according to the present invention has not been seen in any publications, and the process can be easily practiced by those skilled in the art. The strength and the density of the alumina material according to the present invention are higher than those of the conventional alumina material.

While the invention has been described in terms of what are presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A process for producing an alumina material with high strength comprising steps of:
    a) providing an aqueous solution containing a dispersing agent;
    (b) mixing a θ-alumina powder and an α-alumina powder with said aqueous solution to form a slurry, wherein said α-alumina powder has a content range from 1.0 to 20.0 wt. %;
    (c) filtering said slurry to form a green part;
    (d) drying said green part; and
    (e) densifying said dried green part to form said alumina material.

2. The process according to claim 1 wherein said θ-alumina powder has a purity higher than 99.6%.

3. The process according to claim 2 wherein said θ-alumina powder has a specific surface area larger than 32.0 $m^2/g$.

4. The process according to claim 3 wherein said θ-alumina powder has an average diameter smaller than 0.4 μm.

5. The process according to claim 1 wherein said α-alumina powder has an average diameter smaller than 1.0 μm.

6. The process according to claim 1 wherein said dispersing agent is one of a semicarbazide hydrochloride (S-HCl) and an ammonium salt of polymethacrylic acid (PMAA-N).

7. The process according to claim 1 wherein in said step (d), said slurry is filtered under a pressure ranged from 2.5 to 40.0 atm.

8. The process according to claim 7 wherein said pressure is an air pressure.

9. The process according to claim 1 wherein said step (e) is executed by sintering at a temperature ranged from 1500 to 1600° C. for 1 to 4 hours.

10. The process according to claim 1 wherein said alumina material has a relative density over 98.5%, a average strength over 450 MPa, an average grain size less than 4 μm and an equi-axial crystalline microstructure.

11. A process for producing an alumina artificial skeleton with high strength comprising steps of:
   (a) providing an aqueous solution containing a dispersing agent;
   (b) mixing a θ-alumina powder and a nucleation-controlling agent with said aqueous solution to form a slurry, wherein said slurry has an α-alumina powder content in a range from 1.0 to 20.0 wt. %;
   (c) filtering said slurry to form a green part;
   (d) drying said green part; and
   (e) sintering said dried green part to form said alumina artificial skeleton.

12. The process according to claim 11 wherein said θ-alumina powder has a purity higher than 99.6%, a specific surface area larger than 32.0 m$^2$/g, and an average diameter smaller than 0.4 μm.

13. The process according to claim 11 wherein said nucleation-controlling agent is an α-alumina powder.

14. The process according to claim 11 wherein said dispersing agent is one of a semicarbazide hydrochloride (S-HCl) and an ammonium salt of polymethacrylic acid (PMAA-N).

15. The process according to claim 11 wherein said step (d) is executed at a pressure ranged from 2.5 to 40.0 atm.

16. The process according to claim 11 wherein said step (e) is executing at a temperature ranged form 1500 to 1600° C. for 1 to 4 hours.

17. A process for producing an alumina artificial skeleton with high strength comprising steps of:
   (a) providing an aqueous solution containing a dispersing agent;
   (b) mixing a θ-alumina powder and a nucleation-controlling agent with said aqueous solution to form a slurry, wherein said slurry has an α-alumina powder content in a range from 1.0 to 20.0 wt. %;
   (c) pouring said slurry into a mold having a shape of said artificial skeleton;
   (d) filtering said slurry to form a green part;
   (e) releasing said green part from said mold;
   (f) drying said green part; and
   (g) sintering said dried green part to form said high strength alumina artificial skeleton.

18. The process according to claim 17 wherein said nucleation-controlling agent is an α-alumina powder.

19. The process according to claim 17 wherein said artificial skeleton is a head of a hipjoint.

* * * * *